(12) United States Patent
Faucher et al.

(10) Patent No.: US 8,343,715 B2
(45) Date of Patent: Jan. 1, 2013

(54) PHOTOCHROMIC POLYESTERS AND METHODS OF PRODUCING PHOTOCHROMIC POLYESTERS

(75) Inventors: Santiago Faucher, Oakville (CA); Gabriel Iftime, Mississauga (CA); Kentaro Morimitsu, Mississauga (CA); Adela Goredema, Mississauga (CA); Jordan H. Wosnick, Toronto (CA)

(73) Assignee: Xerox Corporation, Norwalk, CT (US)

( * ) Notice: Subject to any disclaimer, the term of this patent is extended or adjusted under 35 U.S.C. 154(b) by 51 days.

(21) Appl. No.: 12/938,737

(22) Filed: Nov. 3, 2010

(65) Prior Publication Data
US 2012/0108775 A1 May 3, 2012

(51) Int. Cl.
*G03C 5/00* (2006.01)

(52) U.S. Cl. ............... 430/345; 430/137.15; 430/109.4; 430/332; 528/271; 528/272; 528/308.3; 502/7

(58) Field of Classification Search ............ 528/271, 528/272, 274, 308.3, 301, 307, 403, 408, 528/354; 503/200, 202, 224; 524/320; 534/573, 534/621, 649; 523/1, 161; 430/137.14, 137.15, 430/109.4, 332, 345; 502/7
See application file for complete search history.

(56) References Cited

U.S. PATENT DOCUMENTS

| | | | |
|---|---|---|---|
| 5,231,135 A | 7/1993 | Machell et al. | |
| 5,621,022 A | 4/1997 | Jaeger et al. | |
| 6,221,137 B1 | 4/2001 | King et al. | |
| 6,472,523 B1 | 10/2002 | Banning et al. | |
| 6,476,219 B1 | 11/2002 | Duff et al. | |
| 6,547,380 B2 | 4/2003 | Smith et al. | |
| 6,576,747 B1 | 6/2003 | Carlini et al. | |
| 6,576,748 B1 | 6/2003 | Carlini et al. | |
| 6,590,082 B1 | 7/2003 | Banning et al. | |
| 6,646,111 B1 | 11/2003 | Carlini et al. | |
| 6,663,703 B1 | 12/2003 | Wu et al. | |
| 6,673,139 B1 | 1/2004 | Wu et al. | |
| 6,696,552 B2 | 2/2004 | Mayo et al. | |
| 6,713,614 B2 | 3/2004 | Carlini et al. | |
| 6,726,755 B2 | 4/2004 | Titterington et al. | |
| 6,755,902 B2 | 6/2004 | Banning et al. | |
| 6,821,327 B2 | 11/2004 | Jaeger et al. | |
| 6,958,406 B2 | 10/2005 | Banning et al. | |
| 7,053,227 B2 | 5/2006 | Jaeger et al. | |
| 7,381,831 B1 | 6/2008 | Banning et al. | |
| 7,427,323 B1 | 9/2008 | Birau et al. | |
| 2006/0022176 A1* | 2/2006 | Wang et al. | 252/583 |
| 2010/0081076 A1 | 4/2010 | Wosnick | |

OTHER PUBLICATIONS

Takwa et al., "Single-Step, Solvent-Free Enzymatic Route to #,#-Functionalized Polypentadecalactone Macromonomers," Macromolecules, Jun. 26, 2008, pp. 5230-5236, vol. 41, No. 14.
Varma et al., "Enzyme Catalyzed Synthesis of Polyesters," Progress in Polymer Science, Aug. 10, 2005, pp. 949-981, vol. 30.
U.S. Appl. No. 12/879,587, filed Sep. 10, 2010.

* cited by examiner

*Primary Examiner* — Frances Tischler
(74) *Attorney, Agent, or Firm* — Oliff & Berridge, PLC

(57) ABSTRACT

A method for producing a photochromic polyester, the method including: a) providing a reaction solution having at least one ester monomer, a photochromic compound having or functionalized to have at least one hydroxyl group, and a metal-free catalyst; b) reacting the at least one ester monomer and the photochromic compound using the metal-free catalyst to produce a polymeric product, where the polymeric product has a photochromic polyester; and c) separating the polymeric product from the reaction solution. A photochromic polyester includes a photochromic compound covalently linked to a polyester and the polyester is obtained by polymerizing a lactone.

11 Claims, No Drawings

PHOTOCHROMIC POLYESTERS AND METHODS OF PRODUCING PHOTOCHROMIC POLYESTERS

RELATED APPLICATION

U.S. patent application Ser. No. 12/879,587, filed Sep. 10, 2010, the disclosure of which is hereby incorporated by reference in its entirety, describes a method of covalently linking colorants to polyesters using enzymatic polymerization and colorant-polyesters produced using the enzymatic polymerization.

TECHNICAL FIELD

The present disclosure generally relates to methods for producing a photochomic polyester using enzymatic polymerization. Specifically, the present disclosure relates to methods of covalently linking a photochromic compound to a polymer. Also disclosed herein are photochromic polyesters produced using the enzymatic polymerization methods.

BACKGROUND

Condensation polymerization methods use high temperatures, high vacuum and metal catalysts that are toxic. In particular, the preparation of polymers by condensation polymerization methods takes several days, and relies on high temperatures (T>200° C.) and low pressures (p<1 mmHg) to drive the polymerization to completion. As condensation polymerization methods operate at temperatures of greater than 200° C. and many photochromic compounds degrade above temperatures of 150° C., condensation polymerization methods can lead to degradation of photochromic compounds and are not suitable to produce photochromic polyesters. Additionally, condensation polymerization methods are not suitable for polymerizing lactones.

What is desired is a method for producing photochromic polyesters that are achieved by relatively low temperatures and would therefore minimize photochromic compound degradation. Such a result is particularly desirable given the high cost of photochromic compounds. Furthermore, biodegradable polyesters for biomedical applications that are free of toxic catalysts are highly valuable but are difficult to produce.

SUMMARY

The present disclosure addresses these and other needs, by providing a low temperature, metal-free polymerization method for producing a photochromic polyester, where a photochromic compound is covalently linked to a polyester.

In embodiments, a method for producing a photochromic polyester, the method comprising the steps of: a) providing a reaction solution comprising at least one ester monomer, a photochromic compound having or functionalized to have at least one hydroxyl group, and a metal-free catalyst; b) reacting the at least one ester monomer and the photochromic compound using the metal-free catalyst to produce a polymeric product, wherein the polymeric product comprises a photochromic polyester; and c) separating the polymeric product from the reaction solution.

In embodiments, a photochromic polyester comprises a photochromic compound and a polyester, wherein the photochromic compound is covalently linked to the polyester and the polyester is obtained by polymerizing a lactone using a metal-free catalyst.

EMBODIMENTS

As used herein, a "photochromic polyester" refers to a photochromic compound covalently linked to a polyester through enzymatic reaction of monomers such as lactones or similar esters. A "photochromic compound" is a compound that is capable of photochromism, which is a reversible transformation of a chemical species between two forms induced in one or both directions by the absorption of electromagnetic radiation, where the two forms have different absorption spectra.

The present disclosure includes a process for the enzymatic polymerization of monomers with a photochromic compound performed at atmospheric pressure and relatively low temperatures, such as, for example, from about 40° C. to about 100° C., or from about 50° C. to about 90° C., or from about 60° C. to about 80° C. As such, the enzymatic polymerization may be accomplished at a lower temperature and without significant, or without any, degradation of the photochromic compound.

The above process is accomplished by: a) providing a reaction solution comprising at least one ester monomer, a photochromic compound having or functionalized to have at least one hydroxyl group, and a metal-free catalyst: b) reacting the at least one ester monomer and the photochromic compound using the metal-free catalyst to produce a polymeric product, wherein the polymeric product comprises a photochromic polyester; and c) separating the polymeric product from the reaction solution.

Photochromic Compounds

The photochromic polyester comprises a photochromic compound covalently bound to a polyester through enzymatic reaction of monomers such as lactones or similar esters.

In embodiments, the photochromic compound used in this disclosure is reactive with an ester monomer while still retaining photochromic functionality even after reaction. This may be achieved with a photochromic compound having at least one reactive end group. An example of a reactive group of a photochromic compound is a reactive hydroxyl group. Thus, any photochromic compound with a reactive group, in particular a reactive hydroxyl group, may be used. For example, any photochromic compound that can be utilized in the enzymatic polymerization of lactones or other ester-forming monomers is suitable, so long as the primary reactive group, such as hydroxyl, is attached to the photochromic compound.

Photochromic compounds exhibit photochromism, which is a reversible transformation of a chemical species induced in one or both directions by absorption of an electromagnetic radiation between two forms having different absorption spectra. The first form is thermodynamically stable and may be induced by absorption of light such as ultraviolet light to convert to a second form. The reverse reaction from the second form to the first form may occur, for example, thermally, or by absorption of light such as visible light, or both. Various exemplary embodiments of the photochromic compound may also encompass the reversible transformation of the chemical species among three or more forms in the event it is possible that reversible transformation occurs among more than two forms. The photochromic compound of embodiments may be composed of one, two, three, four, or more different types of photochromic compounds, each of which has reversibly interconvertible forms. As used herein, the term "photochromic compound" refers to all molecules of a specific species of the photochromic compound, regardless of their temporary isomeric forms. For example, where the photochromic compound is the species spiropyran, which exhibits isomeric forms as spiropyran and merocyanine, at any given moment the molecules of the photochromic compound may be entirely spiropyran, entirely merocyanine, or a mixture of spiropyran and merocyanine. In various exemplary embodiments, for each type of photochromic compound, one form may be colorless or weakly colored and the other form may be differently colored.

An example of a suitable photochromic compound is bis-hydroxymethyl photochrome having the below chemical formula. Additional photochromic compounds may be any commercially available photochromic compounds including hydroxyl groups or photochromic compounds functionalized to include reactive hydroxyl groups.

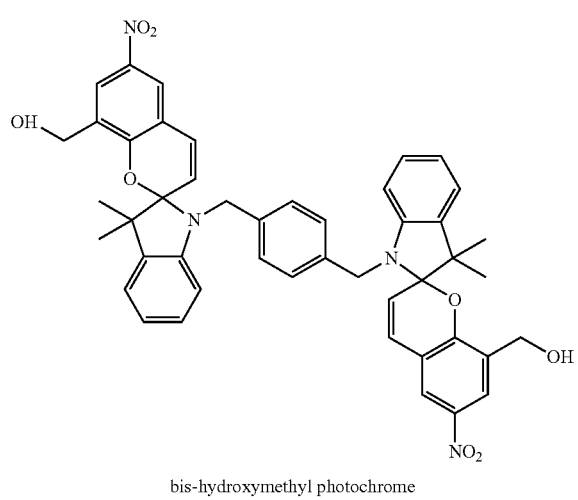 [SMILES: CC1(C)c2ccccc2N(Cc2ccc(CN3c4ccccc4C(C)(C)C34C=Cc3cc([N+](=O)[O-])cc(CO)c3O4)cc2)C12C=Cc1cc([N+](=O)[O-])cc(CO)c1O2]

bis-hydroxymethyl photochrome

Other examples of photochromic compounds include spiropyrans and related compounds like spirooxazines and thiospiropyrans, benzo and naphthopyrans (chromenes), stilbene, azobenzenes, thioindigos, bisimidazols, spirodihydroindolizines, quinines, perimidinespirocyclohexadienones, viologens, fulgides, fulgimides, diarylethenes, hydrazines, anils, aryl disulfides, aryl thiosulfonates, spiroperimidines, triarylmethanes, and the like. In the aryl disulfides and aryl thiosulfonates, suitable aryl groups include phenyl, naphthyl, phenanthrene, anthracene, substituted groups thereof, and the like. These compounds can variously undergo heterocyclic cleavage, such as spiropyrans and related compounds; undergo homocyclic cleavage such as hydrazine and aryl disulfide compounds; undergo cis-trans isomerization such as azo compounds, stilbene compounds and the like; undergo proton or group transfer phototautomerism such as photochromic quinines; undergo photochromism via electro transfer such as viologens; and the like. Specific examples of compounds include:

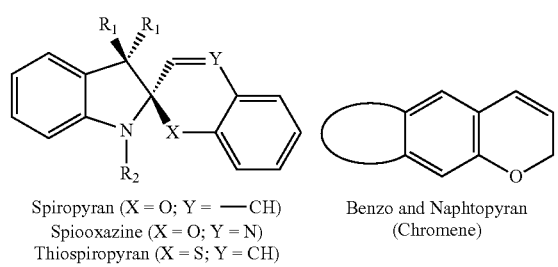

Spiropyran (X = O; Y = —CH)
Spiooxazine (X = O; Y = N)
Thiospiropyran (X = S; Y = CH)

Benzo and Naphtopyran (Chromene)

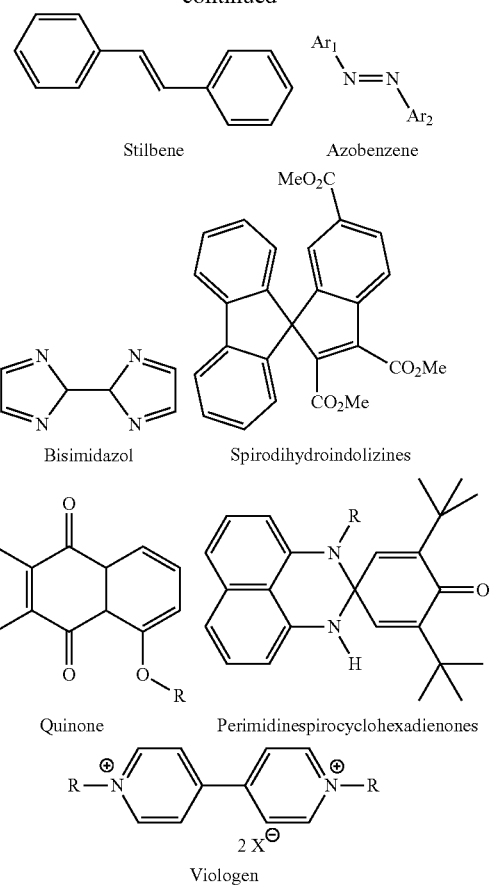

Stilbene
Azobenzene
Bisimidazol
Spirodihydroindolizines
Quinone
Perimidinespirocyclohexadienones
Viologen

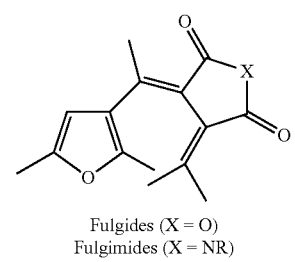

Fulgides (X = O)
Fulgimides (X = NR)

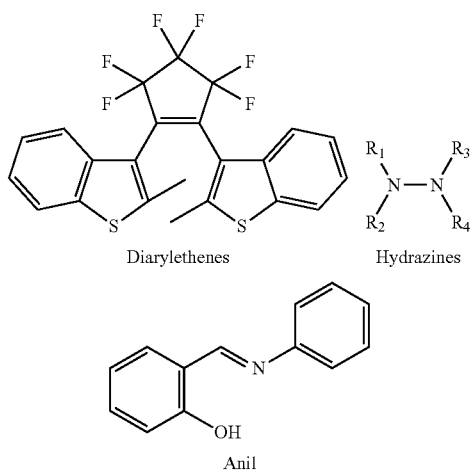

Diarylethenes
Hydrazines
Anil

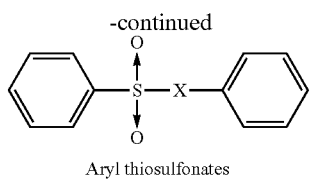

Aryl thiosulfonates

In these structures, the various R groups (i.e., R, $R_1$, $R_2$, $R_3$, $R_4$) can independently be any suitable group including but not limited to hydrogen; alkyl, such as methyl, ethyl, propyl, butyl, and the like, including cyclic alkyl groups, such as cyclopropyl, cyclohexyl, and the like, and including unsaturated alkyl groups, such as vinyl ($H_2C$=CH—), ally ($H_2C$=CH—$CH_2$—), propynyl (HC≡CH—$CH_2$—), and the like, where for each of the foregoing, the alkyl group has from 1 to about 50 or more carbon atoms, such as from 1 to about 30 carbon atoms; aryl, including phenyl, naphthyl, phenanthrene, anthracene, substituted groups thereof, and the like, and having from about 6 to about 30 carbon atoms such as from about 6 to about 20 carbon atoms; heteroaryl, including furyl, thienyl, pyrrolyl, pyridyl, thiazolyl, oxazolyl, and the like; arylalkyl, such as having from about 7 to about 50 carbon atoms such as from about 7 to about 30 carbon atoms; silyl groups; nitro groups; cyano groups; halide atoms, such as fluoride, chloride, bromide, iodide, and astatide; amine groups, including primary, secondary, and tertiary amines; hydroxy groups; alkoxy groups, such as having from 1 to about 50 carbon atoms such as from 1 to about 30 carbon atoms; aryloxy groups, such as having from about 6 to about 30 carbon atoms such as from about 6 to about 20 carbon atoms; alkylthio groups, such as having from 1 to about 50 carbon atoms such as from 1 to about 30 carbon atoms; arylthio groups, such as having from about 6 to about 30 carbon atoms such as from about 6 to about 20 carbon atoms; aldehyde groups; ketone groups; ester groups; amide groups; carboxylic acid groups; sulfonic acid groups; and the like. The alkyl, aryl, and arylalkyl groups can also be substituted with groups such as, for example, silyl groups; nitro groups; cyano groups; halide atoms, such as fluoride, chloride, bromide, iodide, and astatide; amine groups, including primary, secondary, and tertiary amines; hydroxy groups; alkoxy groups, such as having from 1 to about 20 carbon atoms such as from 1 to about 10 carbon atoms; aryloxy groups, such as having from about 6 to about 20 carbon atoms such as from about 6 to about 10 carbon atoms; alkylthio groups, such as having from 1 to about 20 carbon atoms such as from 1 to about 10 carbon atoms; arylthio groups, such as having from about 6 to about 20 carbon atoms such as from about 6 to about 10 carbon atoms; aldehyde groups; ketone groups; ester groups; amide groups; carboxylic acid groups; sulfonic acid groups; and the like. $Ar_1$ and $Ar_2$ can independently be any suitable aryl or aryl-containing group including but not limited to phenyl, naphthyl, phenanthrene, anthracene, and the like, and substituted groups thereof including any of the substitutions mentioned above for the alkyl, aryl, and arylalkyl groups. X in the spiropyran formula is a suitable heteroatom such as N, O, S, and the like. Y can be —N— or —CH—. $X^-$ in the Viologen formula can be, for example, $F^-$, $Cl^-$, $Br^-$, $I^-$, $BF_4^-$, $PF_6^-$, $B(C_6H_5)_4^-$ and the like. $X^-$ in the aryl thiosulfonate can be, for example, —O—, S, —NH— and the like.

In addition to organic compounds, photochromic phenomena is also observed in inorganic compounds, such as metal oxides, alkaline earth metal sulfides, titanates, mercury compounds, copper compounds, minerals, transition metal compounds such as carbonyls, and the like.

In embodiments, the photochromic compound may be linked at the α-position or at the center of the polyester chain. The photochromic compound linked at the center of the polyester chain refers to a photochromic compound having an ester monomer chain chemically linked to a terminal end and at least a second ester monomer chain chemically linked to another terminal end. For example, in some materials having photochromic compounds, small molecule photochromic compounds are simply dispersed in a polymeric binder. For this reason, there is enough mobility of the molecules to undesirably or prematurely relax back from the colored state to the clear state over time. This fading reaction requires geometrical change, which in turn is made easier by increased mobility in the medium. In order to significantly slow down the fading and thus provide a longer-lasting image, it is desired to reduce mobility of the photochromic compound. The photochromic polyester may reduce fading. Because the photochromic compound is attached to the polyester chain, the mobility of the photochromic compound is reduced, as a result, the undesired fading reaction is significantly slowed down or eliminated. The photochromic compound being inserted in the center of a polyester chain further reduces the undesired fading reaction and increases the write life of the photochromic compound.

Ester Monomers

In embodiments, the reaction solution includes an ester monomer. The ester monomer may be a cyclic ester monomer. Any appropriate cyclic ester monomer may be used in the enzymatic polymerization, such as a cyclic ester having from 5 to 16 carbon atoms, such as 6 to 15 carbon atoms, 7 to 12 carbon atoms, or 8 to 10 carbon atoms. For example, the cyclic ester monomer may be a lactone, lactide and macrolide, cyclic carbonate, cyclic phosphate, cyclic depsipeptide or oxirane. Illustrative examples of lactones include oxacycloheptadec-10-en-2-one (available as AMBRETTOLIDE, from Penta Manufacturing Co.), omega-pentadecalactone (available as EXALTOLIDE, from Penta Manufacturing Co.), pentadecalactone, 11/12-pentadecen-15-olide (also known as pentadecenlactone), hexadecenlactone and caprolactone. Other suitable ester monomers include β-propiolactone, β-butyrolactone, propylmalolactonate, 2-methylene-4-oxa-12-dodecanolide, poly(butadiene-b-pentadecalactone, poly(butadiene-b-ε-CL), ε-caprolactone, (R) and (S)-3-methyl-4-oxa-6-hexanolide, 1,3-dioxane-2-one, 1,4-dioxane-2-one, 3(S)-isopropylmorpholine-2,5-dione, Morpholine-2,5-dione derivatives, trimethylene carbonate, 1-methyl trimethylene carbonate, 8-octanolide, δ-Decalactone, 12-Dodecanolide, α-Methylene macrolides, and α-Methylene-δ-valerolactone.

In embodiments, the reaction solution may include a non-cyclic ester monomer. Exemplary non-cyclic ester monomers include diacids, hydroxyl acids, and diesters. For example, suitable non-cyclic ester monomers that may be used include 10-hydroxy decanoic acid, 6-hydroxyhexanoic acid, 10-hydroxyhexadecanoic acid, 12-hydroxydodecanoic acid, 16-hydroxyhexadecanoic acid, 3-hydroxy butyric acid, divinyl dicarboxylates, such as divinyl adipate and divinyl sebacate, 2,2,2-trichloroethyl ester, 2,2,2-trifluoroethyl ester, unactivated diacids, such as succinic, glutaric, adipic and sebacic acids, 6-6'-O-divinyl adipate, α-ω-dixacarboxylic methyl ester, bis(hydroxylmethyl)butyric acid, and ω-fluoro-(ω-1)hydroxyl alkanoic acid.

The ester monomer may be provided to the reaction solution independently, or in the form of an aqueous solution comprising an ester monomer.

The molar ratio of photochromic compound to ester monomer in the reaction solution may be any effective ratio, such as about 1:1 to about 1:50, about 1:10 to about 1:30, about 1:15 to about 1:25, 1:20 to about 1:40, and about 1:20 to about 1:50. Variation in concentration of colorant to ester monomer can be used to control the molecular weight of the polymeric product.

Catalysts

The reaction solution further includes one or more appropriate metal-free catalysts, such as enzymatic catalysts. The enzymatic catalysts catalyze the reaction of a colorant and an ester monomer, and allow the polymerization to occur at low temperatures. An illustrative example of enzymes that can be used is a lipase, such as lipase PA, lipase PC, lipase PF, lipase A, lipase CA, lipase B (such as *candita antartica* lipase B), lipase CC, lipase K, lipase MM, cutinase or porcine lipase. Other exemplary catalysts that may be used are organic catalysts including peroxide catalysts, such as benzoyl peroxide, and azo catalysts, such as azobisisobutyronitrile, and the like.

The catalysts may be present in the reaction solution in immobilized or supported (non-covalently bound enzymes, such as adsorbed enzymes or enzymes that are cross-linked to other enzymes) or both immobilized and supported or free form.

The enzymatic catalysts may be present in the reaction solution in any effective concentration, such as from about 0.001 g/cm$^3$ to about 0.060 g/cm$^3$, such as from about 0.002 g/cm$^3$ to about 0.050 g/cm$^3$, from about 0.004 g/cm$^3$ to about 0.040 g/cm$^3$, from about 0.005 g/cm$^3$ to about 0.030 g/cm$^3$, from about 0.006 g/cm$^3$ to about 0.020 g/cm$^3$, from about 0.01 g/cm$^3$ to about 0,050 g/cm$^3$. The concentration of the one or more enzymes in the reaction solution may be controlled by varying the ratio of the mass of enzyme to the mass of an immobilizing agent, such as one or more of a cross-linked polymeric network, cross-linked polymeric beads, polymeric packings, membranes, silica-gel, silica beads, sand and zeolites.

Optional Reaction Components

The ester monomer may be provided to the reaction solution independently, or in the form of a monomer solution comprising monomer and a solvent.

The reaction solution may thus also comprise one or more suitable solvents, such as toluene, benzene, hexane and its analogs (such as heptane), and tetrahydrofuran and its analogs (such as 2-methyltetrahydrofuran), and methyl ethyl ketone and its analogs.

The solvent may be mixed with the monomer prior to or after addition of the monomer to the reaction solution. When present, the solvent may be of any appropriate concentration range relative to the content of monomer. For example, the solvent may comprise from 1% to about 99% of the total weight of the solvent and the cyclic monomer, such as from about 10% to about 90%, such as from about 25% to about 75%, such as from about 40% to about 60%, or such as about 50% of the total weight of the solvent and the monomer.

The role of the solvent may be to reduce the viscosity of the reaction medium to enable more facile stirring or pumping of the solution.

Reaction Solution and Conditions

In embodiments, an enzymatic polymerization is accomplished by providing a reaction solution that comprises a photochromic compound, an ester monomer and an enzymatic catalyst. The enzymatic polymerization reaction may further comprise water. The polymerization may be initiated by either water present in the reaction medium or by the hydroxyl groups present on the photochromic compound, or both. Thus, two polyester populations may be created through this mechanism in the absence of dry solvents and monomers: one polyester population having a photochromatic compound attached to it and the other polyester population having an α-hydroxyl group, with no photochromic compound attached to it. The polyester with an α-hydroxyl group is not photochromic. By adjusting the amount of water and concentration of starting materials, the ratio of photochromic to non-photochromic polyesters can be changed.

The enzymatic polymerization can be undertaken at temperatures from about 50° C. to about 90° C., or from about 60° C. to about 90° C., or from about 70° C. to about 90° C., or from about 80° C. to about 90° C., or from about 50° C. to about 60° C., or from about 50° C. to about 70° C., or from about 50° C. to about 80° C., or from about 60° C. to about 80° C.

The method may be achieved through any appropriate enzymatic polymerization technique. The method may include bulk polymerization or solution polymerization, in either batch or continuous reactor configuration. In the later cases, the catalyst is packed in a column reactor and ester monomer is pumped through the catalyst to form polymer continuously. In the former case, the catalyst is added to the kettle and stirred along with the added ester monomer(s). In both cases, the photochromic compound is added as a hydroxyl initiating site for the enzymatic polymerization. The ratio of photochromic compound to ester monomer can be used to control the polymer molecular weight to some degree.

Bulk polymerization in a packed-bed reactor includes a reactor having one or more immobilized or supported enzymes, wherein the packed-bed reactor has an inlet and an outlet, and is fed with a solution of ester monomer and the photochromic compound. The method may further include circulating a solution of the ester monomer and photochromic compound through the packed-bed reactor to generate a solution enriched with photochromic polyester, such that the one or more immobilized or supported enzymes convert the ester monomers and the photochromic compound to photochromic polyester in the packed-bed reactor during circulation, and collecting the solution enriched with photochromic polyester exiting through the outlet.

The packed-bed reactor may include one or more immobilizing agents for immobilizing the enzyme, such as a cross-linked polymeric network, cross-linked polymeric beads, polymeric packings, membranes, silica-gel, silica beads, sand and zeolites.

The reactor may be made from any appropriate material, such as stainless-steel tubing, glass tubing or polymer tubing (such as polyetheretherketone (PEEK) tubing).

The reactor may have any suitable diameter and length. In embodiments, the reactor can have an outer diameter of from about 0.1 cm to about 300 cm, such as from about 10 cm to about 100 cm, and a length of from about 1 cm to about 300 cm.

Bulk polymerization of polyesters in a continuous packed-bed reactor using immobilized enzyme catalysts is further disclosed in U.S. application Ser. No. 12/240,421, which is hereby incorporated herein in its entirety by reference.

The method may also include controlling one or more of molecular weight, polydispersity and conversion ratio of the photochromic compound and ester monomer to photochromic polyester using one or more of residence time of the ester monomer and photochromic compound in the reactor, dimensions of the reactor, composition of the reactor, temperature of the reactor and initiator concentration in the photochromic compound and ester solution. Decreasing the feed rate of the reaction solution to the reactor may cause the residence time of the reaction solution within the reactor to increase, and this in turn may cause an increase in the photochromic compound and ester monomer conversion to photochromic polyester and an increase in the molecular weight of the photochromic polyester product.

The method may include monitoring the photochromic polyester product, solution collected from the outlet of the reactor to monitor the conversion of the photochromic compound and one or more ester monomers to a photochromic polyester product. In embodiments, the monitoring includes collecting the photochromic polyester solution when the product has attained a substantially stabilized molecular weight or desired molecular weight. In embodiments, the monitoring includes collecting and analyzing the product solution to determine molecular weight of the photochromic polyester in the solution. Any suitable technique can be used for the analysis of the photochromic polyester in the solution, such as by gel permeation chromatography (GPC), differential scanning calorimetry (DSC) and nuclear magnetic resonance (NMR).

Gel permeation chromatography of the polyester utilizing a refractive index detector (RI) and a photo-diode-array (PDA) is used to confirm the covalent binding between the photochromic compound and formed polyester. The total polyester population can be observed by the RI detector signal while the sub-population containing the photochromic polyester is observed by the FDA detector.

Following polymerization, the collected photochromic polyester may be precipitated into a solvent, such as methanol, and recovered by filtration to eliminate any residual solvent or ester monomer. The resulting cake may be extracted via any appropriate extraction, such as soxhlet extraction with methanol, to remove any unreacted photochromic compound and unreacted ester monomer from the polyester product. Following this extraction, a polyester with covalently bound photochromic compound and polyester is recovered from the soxhlet thimble and left to dry.

The reactor may provide in-situ filtration because the immobilized catalyst remains in the tube during the reaction, thereby avoiding the additional step of diluting and filtering of the reaction mixture after the polymerization has completed.

Reaction Products: Photochromic Polyesters and Polyesters

In embodiments, the enzymatic polymerization reaction produces a reaction product comprising polymeric mixture (polymeric product). The reaction product may include both photochromic polyesters and polyesters formed without a covalently linked photochromic compound (hereinafter "non-photochromic polyester). The photochromic polyester comprises a photochromic compound and a polyester, where the photochromic compound is covalently linked to the polyester. The photochromic compound may be covalently linked to the polyester at an α-position or at the center of the polyester chain.

The polyester (as a part of photochromic polyester or a non-photochromic polyester) may be formed by polymerization of ester monomers. The structure of the formed polyester is dependent on the monomer(s) used in the reaction. An exemplary structure of a polyester is expressed by the following reaction-structure model:

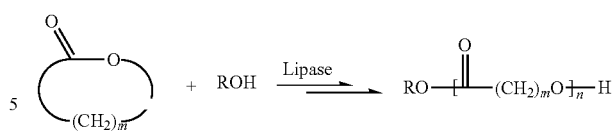

where R may be a photochromic compound, m may be from 4 to 15, such as from 6 to 13, and from 8 to 11, and n may be from 1 to 600, such as from 5 to 200, 10 to 100, and 15 to 25. Other various structures are possible by using any of the ester monomers described above.

A non-photochromic polyester may also be used for its physical, mechanical, rheological, and/or thermal properties. A non-photochromic polyester may, for example, have the desired physical properties for a particular application and, at the same time, serve as a diluent (matrix) for the photochromic polyester. A non-photochromic polyester therefore may help, for example, reduce the concentration of the photochromic polyester in the final product to a concentration desired for a particular application without affecting the other desired properties of the material.

In embodiments, the reaction product may include different photochromic polyesters, with different photochromic compounds linked to different polyester molecules.

The photochromic polyester synthesized using a photochromic compound via the enzymatic polymerization retains its photochromic behavior as observed visually and can be used for various applications that would benefit from material having photochromic characteristics.

Applications

The polymerization method and photochromic polyesters produced by the method may have a wide range of application in various fields. In embodiments, photochromic polyesters may be used, for example, in printing, coatings, biomedical, or sensing industries. For example, the polyester material with the covalently bound photochromic compound could be used as a sensor for laser exposure, which is important in areas such as laser assisted drug delivery. Photochromic polyesters may also be used in inks or toners as they could be incorporated in clear toners so that the toner could be made visible at a later time by shining a UV light onto the paper. A photochromic polyester may be incorporated in polyester powder coatings for automotive applications to permit changes in paint color with weather conditions (e.g. rain vs. shine, night vs. day). The photochromic polyester may also be used as an additive to polymer melts to permit pants or clothing to be made that alters its color with light exposure. Furthermore, the photochromic polyester may be of interest as a means of compatibilizing photochromic compound with a desired matrix for the production of homogenous dispersions or solutions.

Advantages

Enzymatic polymerization methods for producing a photochromic polyester are more environmentally friendly functionalization methods as they are undertaken at low reaction temperatures (about 50° C. to about 90° C.), without use of metal catalysts, under atmospheric pressure, and without solvents or with reduced amounts of solvents. Additionally, the photochromic polyesters may be biodegradable. In embodiments, the enzymatic polymerization methods covalently link a photochromic compound to a polyester at an α-position as at the center of the polyester chain.

Enzymatic polymerization method offers a simple and effective method for functionalizing photochromic compounds. The resulting photochromic polyesters have high compatibility with the polymeric matrices that contain similar polymers, and thus, greatly simplify the incorporation of photochromic compounds into inks or toners without phase separation or precipitation, or need for dispersion. Accordingly, due to their macromolecular structure, photochromic polyesters are more likely to remain dispersed and stable in polymeric matrices of toners or inks.

As enzymatic polymerization methods do not generally require high temperatures, they do not degrade photochromic compounds by minimizing (and preventing) thermal degradation. Additionally, the low temperature used in enzymatic polymerization method is a more environmentally friendly production route than condensation polymerization undertaken at 200° C. or higher. The enzymatic polymerization methods are further environmentally friendly as no metal-based catalysts and solvents are necessary and the photochromic compound may be incorporated into biodegradable polymers produced from ester monomer. It is difficult to obtain biodegradable polymers from ester monomer using other polymerization methods, as enzymes catalyze reactions with high enantio and regio selectivity.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following claims.

EXAMPLES

Illustrative Example

An illustrative example of the enzymatic polymerization reaction is shown in Reaction Diagrams I and II. A photochromic compound may be bound to an ester monomer through enzymatic polymerization method, creating a photochromic polyester. See Reaction Diagram I below.

Reaction Diagram I

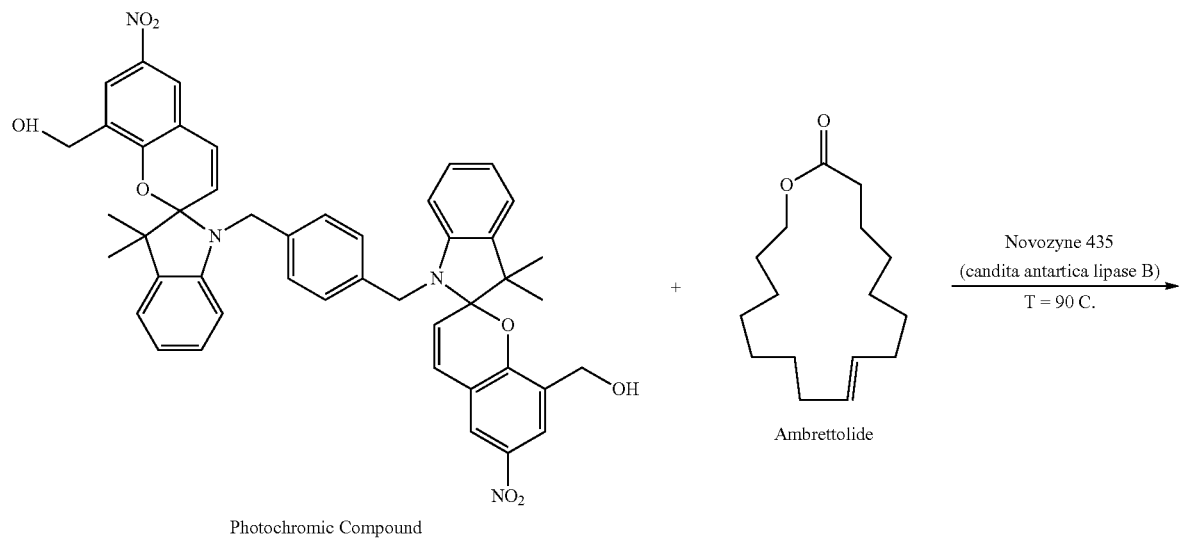

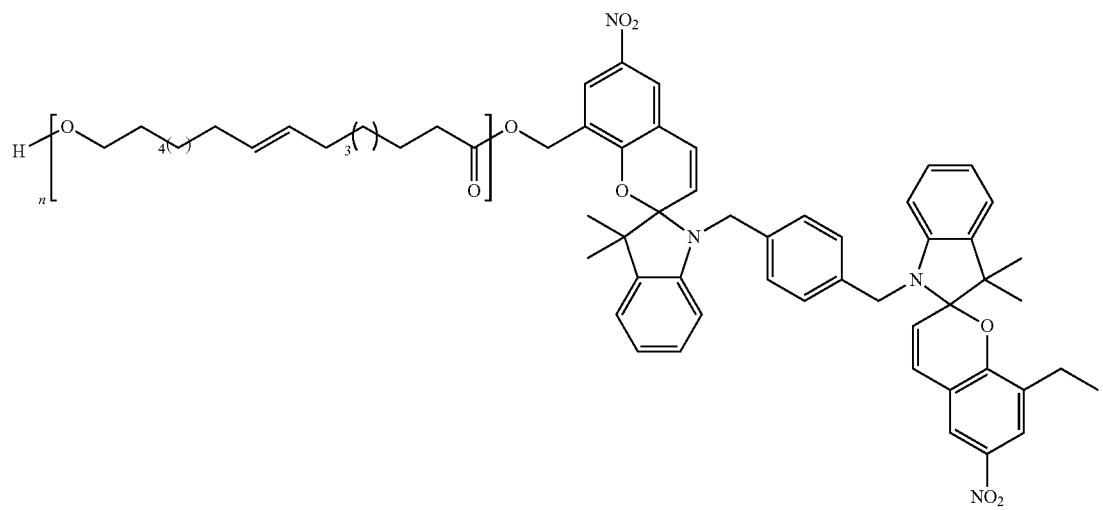

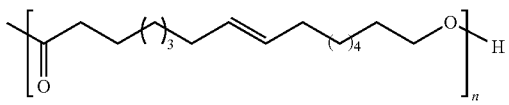

wherein n may be from 1 to 600, such as from 5 to 200, 10 to 100, and 15 to 25.

An ester monomer may also be polymerized through the enzymatic polymerization method initiated by water, optionally present in the reaction system, creating a polyester. See Reaction Diagram II below.

Reaction Diagram II

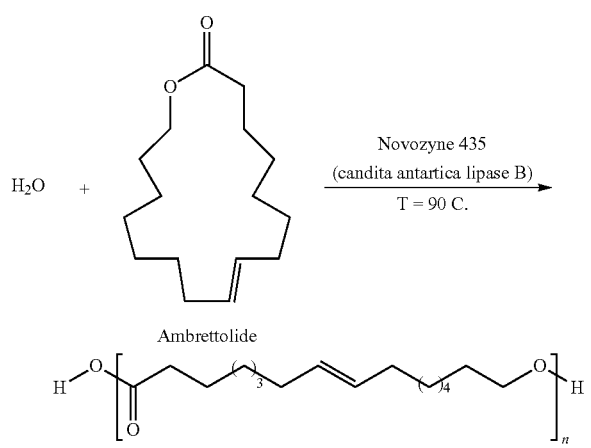

Working Example

Enzymatic Polymerization of Ambrettolide Utilizing a Photochrome Initiating Sight for the Enzymatic Polymerization An example of a suitable photochromic is bis-hydroxymethyl photochrome having the below chemical formula.

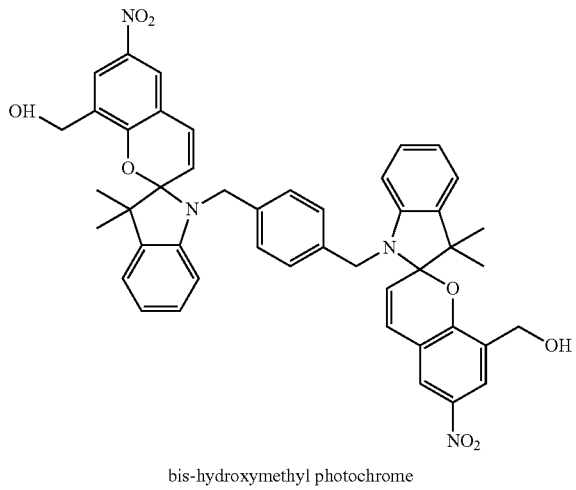 [SMILES: CC1(C)c2ccccc2N(Cc2ccc(CN3c4ccccc4C(C)(C)C34C=Cc3cc([N+](=O)[O-])cc(CO)c3O4)cc2)C12C=Cc1cc([N+](=O)[O-])cc(CO)c1O2]

bis-hydroxymethyl photochrome

Reaction Diagram I summarizes the reaction scheme for the enzymatic polymerization process. Ambrettolide (2.5 g, 0.04 moles), Novozyme 435 (*Candita antartica* Lypase B supported on beads, 0.08 g), MEK (3.1 g), and bis-hydroxymethyl photochrome (0.5 g, 0.0006 moles) were loaded into a 25 ml glass schlenk flask along with a stir bar. The flask was sealed with a rubber septum and then placed in an oil-bath preset to 70° C. so that the monomer may polymerize over 24 hours. Following this period the flask was left to cool and the contents recovered. The solid wax-like material was then dissolved in a small amount of DCM (~10 ml), filtered via vacuum filtration in order to remove the catalyst, and then the filtrate was added to 30 ml of methanol to precipitate the polymer out of solution. The polymer precipitate was recovered via a second vacuum filtration and the retentate loaded to a soxhlet thimble. The material was then soxhlet extracted in methanol to wash the polymer precipitate over 48 hours.

GPC analysis using two independent detectors (PDA and RI) confirmed that the photochromic compound was covalently bound to a part of the polymer population while some polymer was also initiated from free water in the reaction system. Furthermore, this data supports the mechanism of enzymatic polymerization that was utilized by design and outlined in Reaction Diagrams I and II.

The photochromic polyester synthesized using a photochromic compound via the enzymatic polymerization retains its photochromic behavior as observed visually and can be used as a photochromic material for various applications.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for producing a photochromic polyester, the method comprising:
   a) providing a reaction solution comprising at least one ester monomer, a photochromic compound, and an enzymatic catalyst;
   b) reacting the at least one ester monomer and the photochromic compound using the metal-free catalyst to produce a polymeric product, wherein the polymeric product comprises a photochromic polyester; and
   c) separating the polymeric product from the reaction solution, wherein the photochromic compound is bis-hydroxymethyl photochrome having the chemical formula:

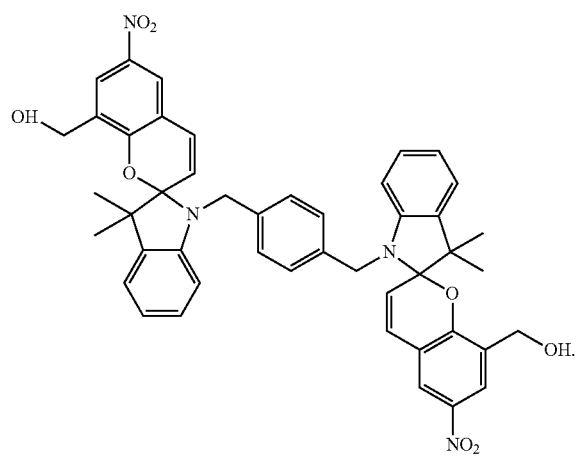 [SMILES: CC1(C)c2ccccc2N(Cc2ccc(CN3c4ccccc4C(C)(C)C34C=Cc3cc([N+](=O)[O-])cc(CO)c3O4)cc2)C12C=Cc1cc([N+](=O)[O-])cc(CO)c1O2]

2. The method of claim 1, wherein the photochromic compound is covalently linked to the photochromic polyester at the center of the photochromic polyester.

3. The method of claim 1, wherein the enzymatic catalyst is one or more members selected from the group consisting of lipase PA, lipase PC, lipase PF, lipase A, lipase CA, lipase B, lipase CC, lipase K, lipase MM, cutinase and porcine lipase.

4. The method of claim 1, wherein step b) comprises heating the reaction solution at a temperature of from about 50° C. to about 90° C.

5. The method of claim 1, wherein the ester monomer is a saturated or unsaturated ester monomer having from 5 to 16 carbon atoms.

6. The method of claim 1, wherein the ester monomer is selected from the group consisting of lactones, lactides, macrolides, cyclic carbonates, cyclic phosphates, cyclic depsipeptides and oxiranes.

7. The method of claim 1, wherein the ester monomer is selected from the group consisting of oxacycloheptadec-10-en-2-one, pentadecalactone, pentadecenlactone, hexadecenlactone and caprolactone, cyclic diester lactide, butyrolactone, propyl malolactone, propiolactone, 1,4-dioxan-2-one, valerolactone, β-propiolactone, β-butyrolactone, 2-methylene-4-oxa-12-dodecanolide, poly(butadiene-b-pentadecalactone, poly(butadiene-b-ε-CL), ε-caprolactone, (R) and (S)-3-methyl-4-oxa-6-hexanolide, 1,3-dioxane-2-one, 1,4-dioxane-2-one, 3(S)-isopropylmorpholine-2,5-dione, Morpholine-2,5-dione derivatives, trimethylene carbonate, 1-methyl trimethylene carbonate, 8-octanolide, δ-Decalactone, 12-Dodecanolide, ω-Pentadecalactone, α-Methylene macrolides, α-Methylene-δ-valerolactone and mixtures thereof.

8. The method of claim 1, wherein the reaction solution further comprises water.

9. The method of claim 1, wherein the photochromic polyester is biodegradable.

10. A method of functionalizing a photochromic compound with an ester or polyester, the method comprising reacting an ester or polyester with a photochromic compound in the presence of an enzymatic catalyst to obtain a photochromic compound functionalized with an ester or polyester, wherein
the photochromic compound is bis-hydroxymethyl photochrome having the chemical formula:

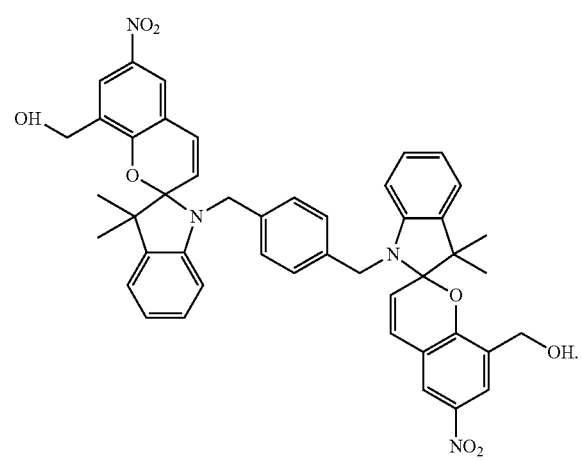 [SMILES: CC1(C)c2ccccc2N(Cc2ccc(CN3c4ccccc4C(C)(C)C34C=Cc3cc([N+](=O)[O-])cc(CO)c3O4)cc2)C12C=Cc1cc([N+](=O)[O-])cc(CO)c1O2]

11. The method of claim 1, wherein the ester monomer is a non-cyclic ester monomer.

* * * * *